United States Patent [19]

Greco et al.

[11] Patent Number: 4,952,619

[45] Date of Patent: Aug. 28, 1990

[54] ORGANIC POLYMER STABILIZATION

[75] Inventors: Alberto Greco, Dresano; Carlo Busetto, S. Donato Milanese; Luigi Cassar, S. Donato Milanese; Carlo Neri, S. Donato Milanese, all of Italy

[73] Assignee: Enichem Synthesis S.p.A., Palermo, Italy

[21] Appl. No.: 50,311

[22] Filed: May 14, 1987

Related U.S. Application Data

[62] Division of Ser. No. 733,526, May 13, 1985, Pat. No. 4,684,726.

[30] Foreign Application Priority Data

May 21, 1984 [IT] Italy ............................ 21023 A/84

[51] Int. Cl.$^5$ .......................... C08K 5/34; C08F 8/00; C08L 83/00
[52] U.S. Cl. ........................... 524/96; 524/99; 524/104; 525/102; 525/103; 525/105
[58] Field of Search .................. 525/105, 103, 102; 524/104, 96, 99; 546/14

[56] References Cited

U.S. PATENT DOCUMENTS

| | | | |
|---|---|---|---|
| 2,644,819 | 7/1953 | Dazzi ............................ | 524/96 |
| 3,209,001 | 9/1965 | Csendes ......................... | 524/96 |
| 3,361,703 | 1/1968 | Childers ........................ | 524/96 |
| 3,673,272 | 6/1972 | Dean ............................ | 525/103 |
| 3,875,254 | 4/1975 | Dean ............................ | 525/103 |
| 4,002,594 | 1/1977 | Fetterman ...................... | 524/96 |
| 4,098,840 | 7/1978 | Yoshida et al. ................. | 525/102 |
| 4,139,519 | 2/1979 | Itoh et al. ..................... | 525/105 |
| 4,141,883 | 2/1979 | Soma et al. .................... | 546/14 |
| 4,201,698 | 5/1980 | Itoh et al. ..................... | 525/105 |
| 4,346,188 | 8/1982 | Costanzi et al. ................ | 524/104 |
| 4,412,038 | 10/1983 | Zerpner et al. ................. | 525/105 |
| 4,617,333 | 10/1986 | Constanzi et al. ............... | 524/96 |
| 4,684,726 | 8/1987 | Greco et al. .................... | 544/69 |

FOREIGN PATENT DOCUMENTS

| | | | |
|---|---|---|---|
| 731223 | 3/1966 | Canada ............................ | 525/102 |
| 0886615 | 11/1971 | Canada ............................ | 525/105 |
| 1196927 | 11/1985 | Canada ............................ | 525/105 |
| 0030649 | 3/1978 | Japan ............................. | 525/105 |

*Primary Examiner*—Kriellion Morgan
*Attorney, Agent, or Firm*—Hedman, Gibson, Costigan & Hoare

[57] ABSTRACT

Reactive stabilizing compounds, able to stabilize organic polymers, contain in their molecule a sterically hindered amino group and a hydrolyzable silyl function.

In stabilizing organic polymers, said reactive stabilizing compounds can be hydrolyzed at the silyl function with the formation of silanol groups, which are made to interact in order to form complex resinous stabilizing structures. These latter are added in stabilizing quantities to the polymer to the stabilized.

According to one particular embodiment, the hydrolysis at the silyl function and the formation of the resinous structure take place spontaneously within the polymer to be stabilized.

According to a further embodiment, the reactive stabilizing compound is added to the polymer after being stably supported on a solid support by reaction with an inorganic solid having surface hydroxyl groups.

According to a further embodiment, the reactive stabilizing compound is made to interact with the polymer so that the stabilizing compound becomes chemically bonded to the polymer chains.

In all cases, stabilized polymers are obtained containing the stabilizing compound in a form which is not removable from the polymer.

The processes for preparing the reactive stabilizing compounds and for preparing the stabilizing polymer compositions are also described.

23 Claims, No Drawings

ORGANIC POLYMER STABILIZATION

This is a divisional of application Ser. No. 733,526 filed May 13, 1985 now U.S. Pat. No. 4,684,726.

This invention relates to reactive stabilising compounds able to stabilise organic polymers, and also relates to the stabilised polymer compositions and the processes for preparing said stabilising compounds and said stabilised polymer compositions.

Organic polymers such as polyolefins and polydienes are known to suffer degradation with the passage of time due to exposure to atmospheric agents, and in particular to the action of ultraviolet radiation. This degradation manifests itself as a worsening of the polymer physical characteristics, such as a reduction in ultimate tensile stress and flexibility, these being accompanied by a change in the viscosity index.

In order to oppose this degradation, it is usual in industry to introduce small quantities of stabilising compounds such as benzotriazoles, benzophenones and nickel complexes into the polymers. Also known for this purpose are pyrrolidine derivatives described in U.S. Pat. Nos. 4,325,364 and 4,346,188 and organic compounds containing in their molecule at least one tetramethyl- or pentamethyl-morpholine, as described in the U.S. patent application Ser. No. 709,546 filed on Mar. 8, 1985 now U.S. Pat. No. 461,733.

The problems encountered in stabilising organic polymers derive essentially from the incompatibility between the stabilising compound and the polymer, and from the release of the stabilising compound by the polymer.

In stabilisation by means of known stabilising compounds, these undesirable phenomena are manifested at a more or less considerable level, and there is therefore a need for stabilising compounds having greater compatibility with the polymers and able to permanently remain therein.

It has now been found that such a requirement can be satisfied by the reactive stabilising compounds of the present invention, which contain in their molecule a sterically hindered amino group and a hydrolysable silyl function.

These reactive stabilising compounds can give rise to complex resinous structures either within the polymer or outside it, or can bond chemically to the polymer or to a solid support. The result of these interactions is that structures are obtained which on the one hand unexpectedly preserve the inherent stabilising characteristics of the sterically hindered amines, and on the other hand present characteristics of compatibility with and permanence in the stabilised polymer which exceed those of the initial reactive stabilising compounds and those of stabilising compounds known in the art.

Accordingly, one object of the present invention is constituted by reactive stabilising compounds containing in their molecule a sterically hindered amino group and a hydrolysable silyl group.

A further object of the present invention is constituted by processes for preparing said reactive stabilising compounds.

A further object of the present invention is constituted by polymer compositions stabilised by the products of the transformation of said reactive stabilising compounds at the silyl function.

A further object of the present invention is constituted by processes for preparing said stabilised polymer compositions.

Further objects of the invention will be more apparent from the description and experimental examples given hereinafter.

In general, the reactive stabilising compounds of the present invention are compounds containing the 2,2,6,6-tetramethylpiperidine group:

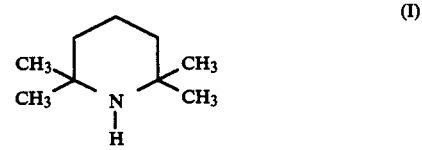

or the 2,2,6,6-tetramethylmorpholine group;

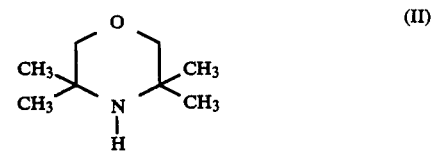

or the 2,2,3,5,5-pentamethylpyrrolidine group;

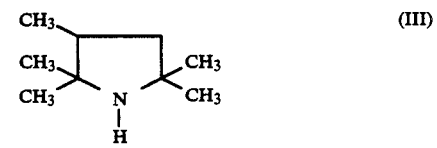

said groups carrying a silyl function which can be hydrolysed to silanol, and is connected to (I), (II) and (III) by a silicon-carbon bond.

More particularly, the reactive stabilising compounds of the present invention can pertain to the following classes of compounds:

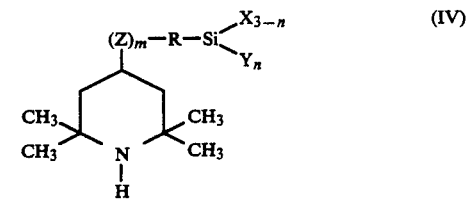

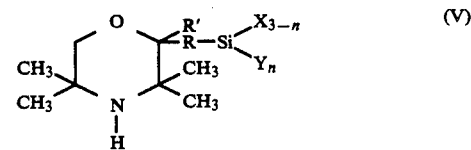

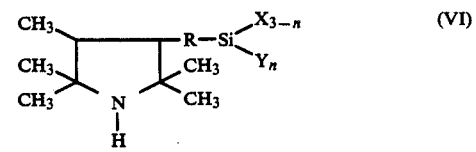

where:
m is zero or one;
R' is hydrogen or methyl;
Z is a group chosen from

(where $R_1$ is a linear or branched alkyl radical containing from 1 to 5 carbon atoms);

R is a linear or branched alkylene radical containing from 1 to 10 carbon atoms, or is representable by:

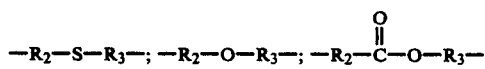

(where $R_2$ and $R_3$ are linear or branched alkylene radical containing a total of between 2 and 10 carbon atoms);

X is a linear or branched alkyl radical containing from 1 to 5 carbon atoms, and preferably the methyl radical;

Y is hydrogen, halogen and preferably chlorine, $C_1$–$C_4$ acyloxy, $C_1$–$C_4$ alkyloxy, amino, amino-oxy or silyloxy, and preferably $C_1$–$C_2$ alkyloxy;

n is one, two or three.

Specific examples of reactive stabilising compounds which fall within formula (IV) are as follows:

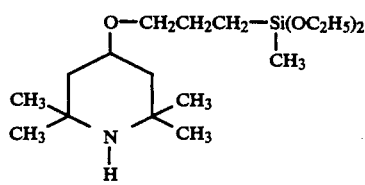

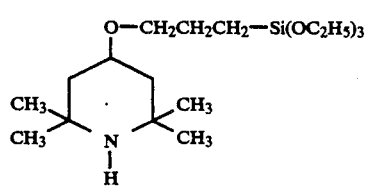

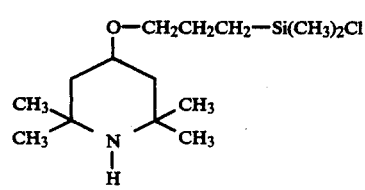

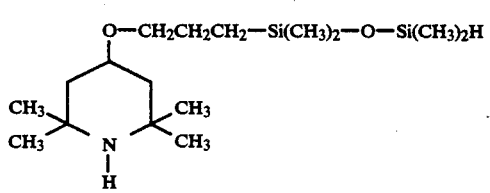

The reactive stabilising compounds (VII), (VIII), (IX) and (X) can be obtained starting from the compound

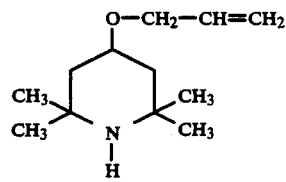

by silylation with methyldiethoxysilane, triethyloxysilane, dimethylchlorosilane and tetramethyldisiloxane respectively.

Further specific examples of reactive stabilising compounds which fall within formula (VI) are the following:

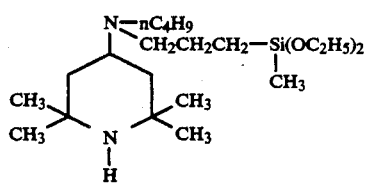

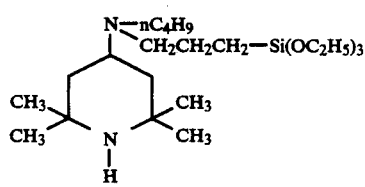

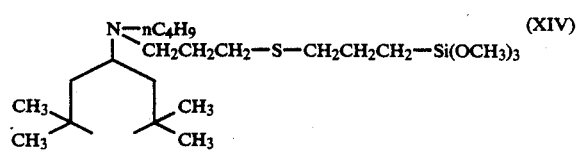

The reactive stabilising compounds (XII), (XIII) and (XIV) can be obtained from the compound:

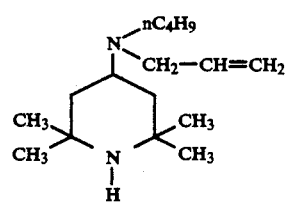

by silylation with methyldiethoxysilane, triethoxysilane and γ-mercaptopropyltrimethoxysilane respectively.

A specific example of a compound which falls within general formula (V) is the following:

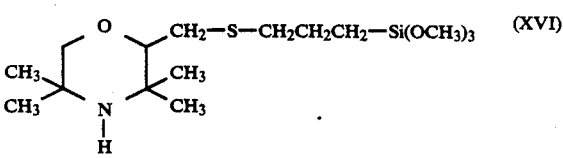

The reactive stabilising compound (XVI) can be obtained by silylation of the compound:

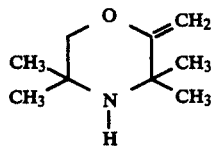

with γ-mercaptopropyltrimethoxysilane.

A specific example of a further compound which falls within general formula (V) is the following:

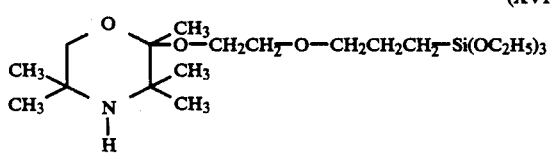

The reactive stabilising compound (XVIII) can be obtained by silylation of the compound:

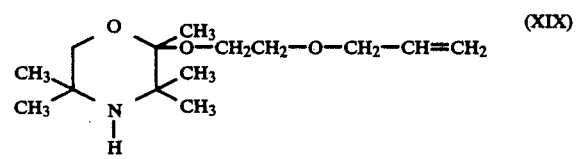

with triethoxysilane.

A specific example of a compound which falls within general formula (VI) is the following:

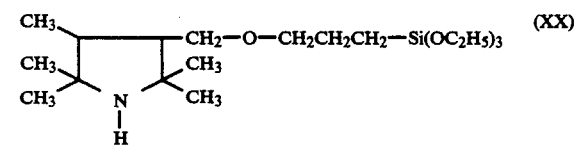

The reactive stabilising compound (XX) can be obtained by silylation of the compound:

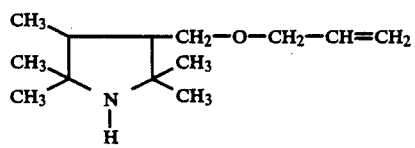

with triethoxysilane.

In general, the reactive stabilising compounds of the present invention can be prepared by silylating a 2,2,6,6-tetramethylpiperidine, or a 2,2,6,6-tetramethylmorpholine, or a 2,2,3,5,5-pentamethylpyrrolidine which carry on their ring a preferably terminal, alkylenically unsaturated bond.

One class of silylation agents suitable for this purpose can be defined by the general formula:

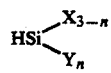 (XXII)

where X, Y and n have the aforesaid meanings.

Specific examples of silylation agents which fall within formula (XXII) are the following:

HSi(CH$_3$)$_2$Cl; HSi(CH$_3$)Cl$_2$; HSiCl$_3$; HSi(CH$_3$)(OCH$_3$)$_2$; HSi(CH$_3$)(OC$_2$H$_5$)$_2$; HSi(OC$_2$H$_5$)$_3$; H$_2$Si(C$_2$H$_5$)$_2$; HSi(OCH$_3$)$_3$; HSi(CH$_3$)$_2$OSi(CH$_3$)$_2$H; HSi(CH$_3$)$_2$OSi(CH$_3$)(OCH$_3$)$_2$; HSi(CH$_3$)$_2$ONC(CH$_3$)$_2$; HSi(CH$_3$)$_2$N(CH$_3$)$_2$; HSi(CH$_3$)(OCOCH$_3$)$_2$; HSi(CH$_3$)[ONC(CH$_3$)$_2$]$_2$.

The silylation reaction is conveniently conducted at a temperature of between 0° and 200° C., and preferably between ambient temperature (20°-25° C.) and 120° C., with a reagent quantity varying from stoichiometric to an excess of the silylation agent. Said excess usually reaches up to 20% on a molar basis. However, if disilanes are used it is convenient to use a large excess of the silylation agent, for example up to 10 times the stoichiometric value.

The silylation reaction is catalysed by metal catalysts, by ultra-violet radiation and by radical initiators. The preferred catalysts are platinum compounds and complexes of platinum with olefins, in particular chloroplatinic acid. In the case of platinum catalysts, the catalyst concentration, evaluated as metal, can vary from 1 to 200 parts per million and preferably from 5 to 50 parts per million in the reaction medium.

The silylation reaction can be conducted in an inert (unreactive) organic solvent, normally chosen from aliphatic, cycloaliphatic and aromatic hydrocarbons and ethers, which are liquid under the operating conditions. Specific examples of solvents suitable for this purpose are heptane, cyclohexane, toluene, tetrahydrofuran, dioxane and dimethoxyethane.

The reaction times depend on the particular reagents used and the reaction temperature, and vary normally from 0.5 to 10 hours.

On termination of the silylation reaction, any solvent used and any excess silylation agent are removed by stripping, and the reactive stabilising compound is recovered from the residue of said stripping by normal methods such as crystallisation and distillation under vacuum.

However, generally the high yield and selectivity of the silylation reaction make any separation or purification of the final required product unnecessary.

A further class of silylation agents suitable for the purpose can be defined by the general formula:

 (XXIII)

where R$_3$, X, Y and n have the aforesaid meanings.

Specific examples of silylation agents falling within formula (XXIII) are γ-mercaptopropyltrialkoxysilanes, and in particular γ-mercaptopropyltrimethoxysilane.

If silylating compounds falling within formula (XXIII) are used, the reaction can be conducted under the aforesaid general silylation conditions, in the presence of catalysts of radical or ionic type, or under the action of ultraviolet radiation. In this case the preferred catalysts are azo compounds, such as azobisisobutyronitrile, which are conveniently used in a quantity of between 0.1% and 10% and preferably between 0.5% and 2% in the reaction environment.

The reactive stabilising compounds of the present invention hydrolyse at the silyl function, under mild conditions, to generate silanol groups which can be condensed together to form complex resinous stabilising structures.

These resinous structures, of silicone resin type, preserve the inherent stabilising characteristics of sterically hindered amines, and have a very high level of compatibility with organic polymers, and practically no extractability from such polymers.

Hydrolysis of the silyl function takes place simply by contact with water or with environmental moisture at ambient temperature (20°-25° C.) or lower than ambient.

Condensation between the silanol groups to give the complex resinous structures can be facilitated by acid or basic agents, soaps and metal esters, and organometal compounds, especially of zinc, lead and tin.

Catalysts suitable for this purpose are zinc octoate, lead naphthenate and tin dibutyl-laurate. Conveniently, the catalyst quantity can vary from 0.1% to 10% by weight and preferably from 0.2% to 3% by weight with respect to the reactive stabilising compound subjected to resinification. Said resinification reaction can be conducted at ambient temperature (20°-25° C.) or at higher or lower than ambient. The complex resinous structure thus obtained can be introduced into the organic polymer to be stabilised by the usual methods used for this purpose.

According to a further embodiment of the present invention, the reactive stabilising compounds are introduced directly into the organic polymer, within which the hydrolysis reaction at the silyl function and the interaction between the silanol groups take place spontaneously, to thus give the stabilised polymer composition.

According to a further embodiment, hydrolysis at the silyl function of the reactive stabilising compounds takes place externally to the polymer, together with partial resinification of the hydrolysis products thus obtained. The product of the partial resinification is then introduced into the organic polymer to be stabilised, within which complete resinification takes place.

According to a preferred embodiment, the reactive stabilising compounds of the present invention are reduced to pigment form, and as such are added to the organic polymer to be stabilised. For this purpose, the reactive stabilising compounds are hydrolysed and resinified by exposure to moisture, possibly in the presence of a catalyst chosen from those described heretofore. The resinification products thus obtained, in the form of vitreous solids and still soluble in aliphatic alcohols, are heated to a temperature exceeding 100° C. and generally of between 120° and 220° C. for a time of between 10 minutes and 6 hours. After cooling, the solid is ground and pulverised, and the powder thus obtained is added to the organic polymer to be stabilised.

According to a further embodiment of the present invention, the reactive stabilising compounds are added to silicone varnishes, such as those available commercially, generally in a hydrocarbon vehicle and co-resinified together with said varnishes, using the actual heat treatment of the varnishes. The resultant vitreous products are ground and pulverised and the powder is added to the organic polymer to be stabilised. In this latter embodiment, a quantity of reactive stabilising compound of between 10% and 90% by weight with respect to the silicone varnish can be used.

In all cases, the powders added to the polymer to be stabilised should have a size of less than 10 microns and preferably of the order of 0.1-2 microns.

The structure of these resinification products depends essentially on the number of groups hydrolysable at the silyl function in the reactive stabilising compounds.

For example in the case of compound (IX), which contains only one hydrolysable group, the hydrolysis and resinification reactions proceed until a dimer is produced, which in the case in question can be defined by the following formula:

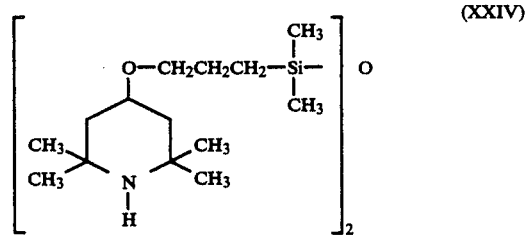

In the case of compounds with two or three hydrolysable groups in the silyl function, more complex resinification products are obtained, in the form of linear and three-dimensional polymer chains respectively.

The reactive stabilising compounds of the present invention can be fixed to a solid support containing surface hydroxyl groups. Supports suitable for this purpose are siliceous materials, of either natural or synthetic origin, such as diatomaceous earth, celite, silica gel, cement, glass, glass fibres and silicon aluminates in general. The preferred of all these supports is that type of silica commonly known as fumed silica which, together with good optical characteristics, has low apparent density, a high specific surface (generally exceeding 200 $m^2/g$) and a high surface concentration of hydroxyl groups.

The bond to the support is produced by reacting the reactive stabilising compound in its hydrolysed form with the surface hydroxyl groups of the support. In practice, the support, in the form of powder or granules, is put into contact with a solution of the reactive stabilising compound in an inert organic solvent, such as an aliphatic cycloaliphatic or aromatic hydrocarbon or an ether. The procedure is carried out in the liquid phase at a temperature between ambient (20°-25° C.) and about 100° C. The reactive stabilising compound becomes hydrolysed and bonded to the support within a time of the order of between 0.5 and 10 hours.

The stabilising compound thus supported is added to the organic polymer to be stabilised, by normal methods. This embodiment has the further advantage of excellent distribution of the stabilising compound in the polymer.

According to a further embodiment, the reactive stabilising compounds of the present invention are bonded chemically to the organic polymer to be stabilised. This method is particularly effective in the case of diolefinic polymers and copolymers of low molecular weight. The reaction between the reactive stabilising compound and the polymer generally takes place at a temperature of between ambient (20°-25° C.) and about 100° C., in the presence of an inert (unreactive) diluent, in a time of between 0.5 and 10 hours.

The reactive stabilising compounds of the present invention are able to stabilise organic polymers in general, and in particular homopolymers and copolymers of olefins and diolefins such as polypropylene, polybutadiene and polyethylene of high and low density, especially towards ultraviolet radiation.

The stabilised polymer compositions of the present invention contain a stabilising quantity of the described stabilising compounds. In particular, the stabilising quantity of a stabilising compound is that which adds to the composition at least 0.003% by weight of active nitrogen, the term "active nitrogen" signifying the nitrogen in the piperidine, morpholine or pyrrolidine ring.

There is no critical upper limit to the qualtity of stabilsing compound present in the composition, however it is preferable to not exceed 0.3% by weight of active nitrogen, both for economy reasons and in order not to cause undesirable changes in one or more characteristics of the organic polymer.

In the preferred embodiment, the polymer compositions of the present invention contain an active nitrogen quantity of between 0.005% and 0.02% by weight, the absolutely preferred values being of the order of 0.010%–0.015% by weight. The following experimental examples are given for illustrative purposes, and do not limit the range of the invention.

EXAMPLE 1

Preparation of compound (XI)

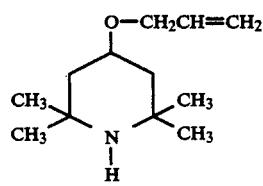
(XI)

Dimethoxyethane (200 ml), tetramethylpiperidinol (47.1 g; 22.6 moles) and metal potassium (13 g; 0.325 g atoms) are fed under a stream of anhydrous nitrogen into a four-neck flask provided with an agitator, thermometer, dropping funnel and reflux condenser.

The suspension is heated under slight reflux for 16 hours under agitation. At the end of this time, not all the potassium has reacted.

The mixture is cooled to 50° C., and allyl bromide (28.6 ml; 4.00 g; 0.33 moles) is slowly added through the dropping funnel, while maintaining the temperature between 50° and 60° C. When the addition is complete, the mass is kept under slight boiling for 30 minutes. A white precipitate of potassium bromide is formed, which is kept in suspension. After said time, a small quantity of methanol (5 ml) is added to eliminate any presence of unreacted metal potassium. After cooling, the suspension is filtered through a sintered glass filter and the separated potassium bromide is washed with 3×50 ml portions of dimethoxyethane.

The liquid wash fractions and the filtrate are pooled and subjected to fractional distillation under vacuum (1 torr) to give the compound (XI)(40.5 g; yield 68.5% evaluated on the fed tetramethylpiperidinol). The compound (XI) thus obtained has a boiling point of 56°–58° C.

Elementary analysis: theoretical: C 73.1%; H 11.7%; N 7.1%; Found: C 73.0%; H 11.5%; N 7.0%.

EXAMPLE 2

Preparation of compound (VII)

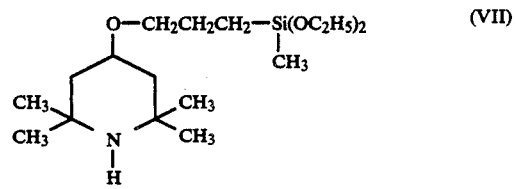
(VII)

The compound (XI) (9.85 g; 50 mmoles) is reacted in a closed vessel with methyldiethoxysilane (8.73 g; 10.5 ml; 65 mmoles) in the presence of traces of chloroplatinic acid dissolved in isopropanol (20 μl of a 2 weight % solution of $H_2PtCl_6.6H_2O$).

The reaction is conducted under agitation at 75° C. for 4 hours and at 100° C. for one hour. At the end of this time, spectroscopic examination shows that the compound (XI) has completely reacted (disappearance of the band at 1645 $cm^{-1}$). The reaction mixture, of oily appearance, is transferred into a Glaisen apparatus, the excess dimethyldiethoxysilane is stripped off under vacuum, and fractionation is carried out to separate 12.7 g of compound (VII) [yield 77% with respect to compound (XI)], having a boiling point of 127°–130° C. (1 torr) and $[n]_D^{20}=1.4439$.

Elementary analysis: theoretical: C 61.6%; H 11.2%; N 4.2%; found: C 62.2%; H 11.2%; N 4.2%.

The structure of the compound (VII) is confirmed by mass spectroscopy (M+ 331) and IR and $^1$Hnmr analysis.

EXAMPLE 3

Preparation of the compound (VIII)

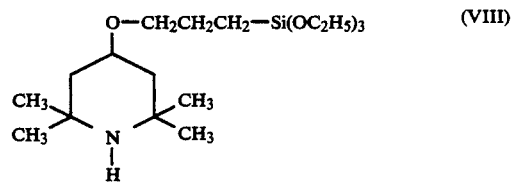
(VIII)

The compound (XI) (5.91 g; 30 mmoles) is reacted with triethyloxysilane (6.6 g; 7.5 ml; 40.0 mmoles) in the presence of traces of chloroplatinic acid in accordance with the procedure of Example 2. On fractionating the reaction product under reduced pressure, 7.2 g of the compound (VIII) are obtained [yield 66.5% with respect to the compound (XI)], having a boiling point of 136°–138° C. (1 torr).

Elementary analysis: theoretical: C 59.8%; H 10.8%; N 3.9%; found: C 60.0%; H 10.8%; N 3.8%.

The structure of the compound (VIII) is confirmed by mass spectroscopy (M+ 361) and IR and $^1$Hnmr analysis.

EXAMPLE 4

Preparation of the compound (IX)

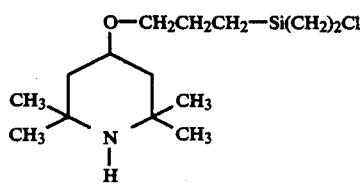
(IX)

The compound (XI) (4.0 g; 22.3. mmoles) is reacted with dimethylchlorosilane (2.85 g; 34 mmoles) in the presence of traces of chloroplatinic acid in accordance with the procedure of Example 2. The reaction mixture thus obtained is stripped under reduced pressure and the resultant oily residue (about 5.5 g) shows no presence of the allyl unsaturation band at 1645 cm$^{-1}$ on IR analysis. The mass spectrum (M+ 291) and elementary analysis (chlorine content 11.7% by weight—theoretical value 12.2% by weight) confirm the structure of the compound (IX) which is used without further purification.

EXAMPLE 5

Preparation of the compound (XXIV)

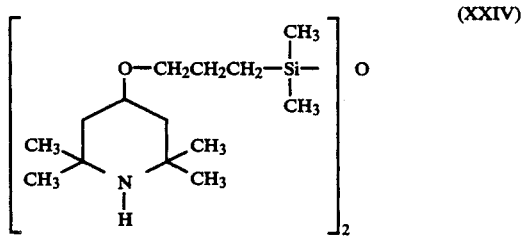
(XXIV)

by hydrolysis and resinification of the compound (IX). The compound (IX), obtained in the preceding Example 4 (4.0 g; 13.6 mmoles) is diluted with diethyl ether, and ice (about 10 g) is added, operating in a flask provided with a magnetic bar agitator. After liquefaction of the ice, the water and organic phases are agitated for two hours at ambient temperature. The ether layer is then separated, washed with aqueous sodium bicarbonate and water, and dried under vacuum to remove the diethyl ether, 1.7 g of an oily residue are obtained in this manner, which on elementary analysis shows the following values: C 62.9%; H 11.5%; N 5.1%; Cl absent.

The theoretical values for the compound (XXIV) are C 63.6%; H 6.4%; N 5.3%. The mass spectrum does not produce the parent ion, but IR and $^1$Hnmr analysis confirm the structure of the compound (XXIV). The aqueous layer is extracted with 2×30 ml portions of chloroform, to allow the recovery of 1.8 g of a product constituted mostly by the compound (XXIV), the remainder consisting of unidentified compounds.

EXAMPLE 7

Preparation of the compound (XII)

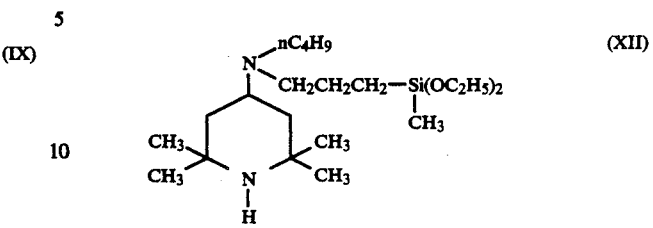
(XII)

The compound (XV)

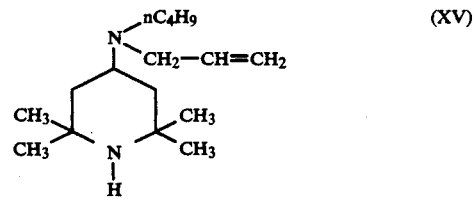
(XV)

(5.0 g; 19.8 mmoles) is reacted under the conditions of Example 1 with methyldiethoxysilane (3.4 g; 4.1 ml; 25 mmoles). The completeness of the reaction is verified by IR analysis on the basis of the total disappearance of the band at 1638 cm$^{-1}$ (allyl band). Fractional distillation under reduced pressure results in the separation of 6.2 g of an oily material [yield 82.4% with respect to the compound (XV)] having a boiling point of 142°–144° C. (1 torr), and consisting of the compound (XII).

Elementary analysis: theoretical: C 65.3%; H 11.9%; N 7.3%; found: C 65.1%; H 11.9%; N 7.3%.

The mass spectrum (M+ 386) and IR and $^1$Hnmr analysis confirm the structure of the compound (XII).

EXAMPLE 8

Preparation of the compound (XIII)

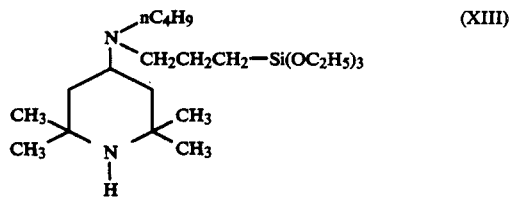
(XIII)

The compound (XV) (6.3 g; 25.0 mmoles) is reacted under the conditions of Example 1 with triethoxysilane (5.6 ml; 4.3 g; 30 mmoles) for 6 hours at 100° C. and for the next 2 hours at 120° C. The reaction mixture is then transferred into a Claisen apparatus and is distilled under vacuum (1 torr) to give 5.3 g of a colourless oil [yield 51% with respect to the compound (XV)], having a boiling point of 147°–149° C. (1 torr) and consisting of the compound (XIII).

Elementary analysis: theoretical: C 63.5%; H 11.5%; N 6.7%; found: C 63.0%; H 11.3%; N 6.2%.

The mass spectrum (M+ 416) and IR and $^1$Hnmr analysis confirm the structure of the compound (XIII).

EXAMPLE 9

Preparation of the compound (XIV)

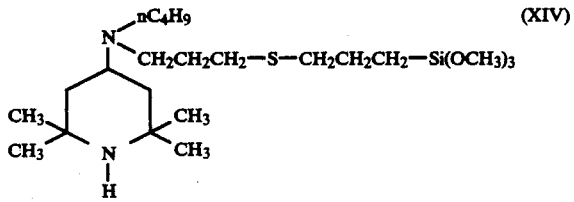 (XIV)

The compound (XV) (3.5 g; 13.8 mmoles) is reacted with slightly more than the stoichiometric quantity of γ-mercaptopropyltrimethoxysilane (3.3 g; 3.2 ml; 17.0 mmoles), together with azobisisobutyronitrile (130 mg) dissolved in 4 ml of toluene, in a flask fitted with a magnetic agitator.

The mixture is agitated for 4 hours at 85° C. and then for the next hour at 110° C. After cooling, the reaction mixture is distilled in a bulb still under reduced pressure (1 torr), and the fraction which distils at a boiler temperature of 230°–235° C. (1 torr) is collected. 3.1 g of a colourless oil are recovered [yield 50% with respect to the compound (XV)], consisting of the compound (XIV).

Elementary analysis: theoretical: C 58.9%; H 10.7%; N 7.1%; found: C 60.1%; H 10.8%; N 6.8%.

The mass spectrum (M+ 448) and IR and ¹Hnmr analysis confirm the structure of the compound (XIV).

EXAMPLE 10

Preparation of the compound (XVI)

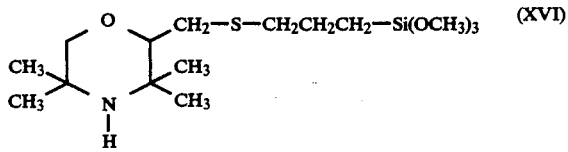 (XVI)

The compound (XVII)

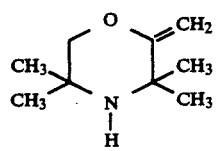 (XVII)

(6.3 g; 40.6 mmoles) is reacted with γ-mercaptopropyltrimethoxysilane (9.8 g; 9.4 ml; 50 mmoles) under the conditions of the preceding Example 9. The reaction mixture is stripped at 60° C. under reduced pressure, and the residue is distilled in a bulb still and the fraction which distils at a boiler temperature of 185°–190° C. (1 torr) is collected. 6.2 g of an oil consisting of the compound (XVI) are recovered.

Elementary analysis: theoretical: C 51.3%; H 9.4%; N 4.0%; S 9.1%; found: C 50.8%; H 9.4%; N 3.9%; S 9.1%.

The mass spectrum (M+ 351) and IR and ¹Hnmr analysis confirm the structure of the compound (XVI).

EXAMPLE 11

Preparation of the hydrolysis and resinification product of the compound (VII)

The compound (VII) (3 g; 9.1 mmoles) is placed in a watch glass together with 30 μl of Sn(n-C₄H₉)₂(laurate)₂.

The glass with its contents is then placed in a controlled-humidity environment (50% relative humidity) at ambient temperature (about 20° C.) for one week.

At the end of this period, the IR spectrum of the product obtained appears substantially changed compared with that of the starting compound (VII). Attempts at distillation with a boiler temperature of 230°–240° C. (1 torr) did not separate any appreciable quantity of volatile products.

EXAMPLE 12

Deposition of the compound (VII) on a fumed silica support 50 g of anhydrous fumed silica (a commercial product of the firm Wacker) with a specific surface of 250 m²/g and apparent density of 0.05 g/ml are placed in 150 ml of boiling n-heptane containing 0.5 g of the compound (VII), the mixture being heated under reflux for 4–5 hours. At the end of this period, the reaction mixture is cooled, filtered, the filtered solid washed with n-pentane, and the washed solid then dried. IR examination of the obtained solid in hexachlorobutadiene shows the presence of a supported organic material, which is not removed by washing with liquid hydrocarbons. The liquid n-pentane and n-heptane fractions are pooled and evaporated to dryness under reduced pressure. 0.140 g of an oil residue are obtained. On the basis of these results it is assumed that about 70% of the compound (VII) was stably supported on the fumed silica.

EXAMPLE 13

Preparation of the compound (X)

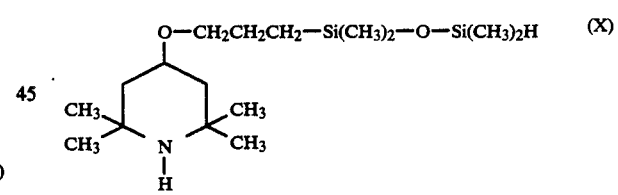 (X)

The compound (XI) (1.3 g; 6.6 mmoles) is reacted with tetramethyldisiloxane (8.86 g; 11.7 ml; 66 mmoles) in the presence of chloroplatinic acid in a manner similar to Example 2.

The operation is carried out in an iso-octanol environment at 80° C. for 4 hours. At the end of this period, the reaction mixture is stripped under reduced pressure to remove the iso-octanol and the excess tetramethyldisiloxane, to give a residue of 2.1 g of the oily compound (X) having a boiling point of 100°–102° C. (0.5 torr), with a Si-H band (IR) at 2120 cm⁻¹.

EXAMPLE 14

Grafting the compound (X) onto liquid polybutadiene

The compound (XI) (1.0 g; 3.0 mmoles) in 10 ml of cyclohexane is added to a commercial liquid polybutadiene of molecular weight 2400 and vinyl content 18.7% (14.4 g; 6 mmoles).

The mixture is heated for 6 hours to 100° C. without adding catalyst. At the end of this period, IR examination shows the absence of Si-H bonds (absence of the band at 2138 cm$^{-1}$) and the consequent bonding of the compound (X) to the liquid polybutadiene.

EXAMPLE 15

An alternative method for producing the compound (XXIV) consists of reacting the compound (VIII) with 1,1,2,2-tetramethyl-1,2-dihydrodisiloxane in the presence of a platinum catalyst The compound (VIII) (4.0 g; 20 mmoles) and 1,1,2,2-tetramethyl-1,2-dihydrosiloxane (1.34 g; 1.72 ml; 10 mmoles) are reacted at 85° C. in the presenece of 10 μl of the catalyst described in Example 2. After a further hour at 100° C., the reaction is complete (disappearance of the Si-H band at 2130 cm$^{-1}$ on IR analysis). After stripping the product under reduced pressure (0.1 torr; 120° C.), 5.2 g of a residue are obtained (yield 97%) in the form of an undistillable oil, constituted by the compound (XXIV).

EXAMPLE 16

Preparation of the compound (XXI)

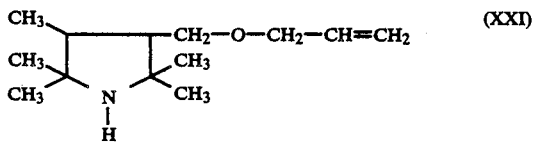

2,2,3,5,5-pentamethyl-4-methylolpyrrolidine (3.1 g; 21.0 mmoles) is reacted with metal potassium (0.88 g; 22.0 m atoms) in dimethoxyethane (50 ml) under reflux for 10 hours.

At the end of this period, the potassium is still present in an unaltered state.

The reaction mixture is cooled to 60° C., and allyl chloride (1.91 g; 2.1 ml; 25.0 mmoles) is carefully added over about 5 minutes. After reaction at 60° C. for one hour, a suspension is obtained and is filtered off through sintered glass, the dimethoxyethane is eliminated by evaporation under reduced pressure at ambient temperature, and the oily residue is distilled under reduced pressure to give 3.3 g of the compound (XXI) (yield 79%; boiling point 58°-60° C., 0.5 torr). The structure of the compound (XXI) is confirmed by mass spectroscopy (M+197) and IR and $^1$Hnmr analysis.

Elementary analysis: theoretical: C 73.1%; H11.7%; N 7.1%; found: C 71.8%; H 11.5%; N 6.9%.

EXAMPLE 17

Preparation of the compound (XX)

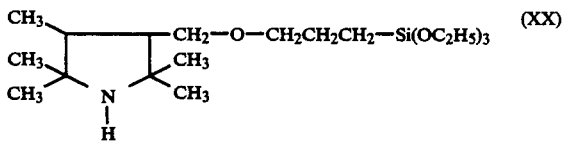

The compound (XXI) (2.5 g; 12.7 mmoles) is reacted at 135° C. with triethoxysilane (2.47 g; 2.8 ml; 15.0 mmoles) for 4 hours in the presence of 10 μl of the catalyst described in Example 2.

On termination of the reaction, the resultant oil is distilled to obtain a fraction having a boiling point of 130°-133° C. at 0.5 torr, and constituting the required compound (XX) (2.8 g; yield 62%). The structure of the compound (XX) is confirmed by mass spectroscopy (M+361) and Ir and $^1$Hnmr analysis.

Elementary analysis: Theoretical; C 60.3%; H 10.8%; N 3.8%; found: C 59.8%; H 101.8%; N 3.9%.

EXAMPLE 18

Preparation of the compound (XIX)

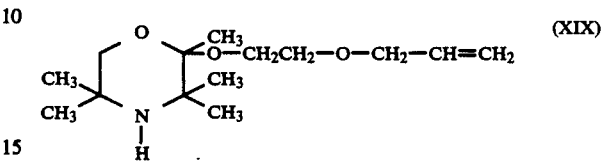

2-methylenetetramethylmorpholine (41.1 g; 26.5 mmoles) and ethyleneglycol monoallylether (2.7 g; 26.5 mmoles) are agitated at 110° C. for 3 hours in the presence of p-toluenesulphonic acid (0.1 g; approximately 1.5% by weight in the reaction mixture). The resultant product is fractionated under vacuum to give the compound (XIX) (4.2 g; yield 62%), with a boiling point of 86°-88° C. at 0.5 torr. The structure of the compound (XIX) is confirmed by mass spectroscopy (M+257) and Ir and $^1$Hnmr analysis.

Elementary analysis: theoretical: C 65.5%; H 10.5%; N 5.4%; found: C 65.4%; H 10.5%; N 5.4%.

EXAMPLE 19

Preparation of the compound (XVIII)

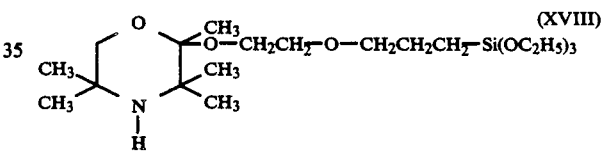

The compound (XIX) (3.5 g; 13.6 mmoles) is reacted with triethoxysilane (2.55 g; 2.8 ml; 15.5 mmoles) at 120° C. for 6 hours in the presence of 10 μl of the catalyst described in Example 2. The reaction products are then distilled togive a fraction having a boiling point of 120°-125° C. at 0.5 torr, and constituted by the required compound (XVIII) (0.7 g; yield 12%). The structure of the compound (XVIII) is confirmed by mass spectroscopy (M+421) and by Ir and $^1$Hnmr analysis.

Elementary analysis: theoretical: C 58.1%; H 10.7%; N 3.1%; found: C 57.0%; H 10.2%; N 3.3%.

EXAMPLE 20

The compound (VIII) (3.5 g) is added to a commercial silicone varnish (DOW CQS-6312) containing 35% of solids in hydroalcoholic solution (18.6 g), the procedure being carried out in a flat-bottomed aluminum capsule of diameter 10 cm, which is then left standing overnight in the environmental atmosphere. The capsule is then heated to 35° C. for 4 hours in an oven to give a transparent glass, which is finally dried in an oven at 130° C. for 4 hours.

The vitreous flakes obtained (8.3 g) are pulverised in a vibration mill to give a white powdery material in which more than 80% of the particles have a diameter equal to or less than 1 micron. The stabilising action of the stabilising compounds of the present invention is verified by laboratory tests capable of simulating olefinic polymer degradation. Specifically, propylene films to which the stabilising compounds have been added are subjected to UV radiation in a photochemical reactor temperature-controlled at 80° C. In this manner, the sample is subjected both to thermal and to photodegradation stresses, during which the oxygen absorbed by the film is measured against time.

The specific apparatus used is constituted by:

a radiation reactor provided with a high-pressure 150 watt mercury vapour lamp emitting light at $\lambda \geq 300$ nm;

a balancing chamber of the same temperature as the reactor, to prevent volume variations due to temperature changes;

a U tube containing mercury and fitted with electric contacts, its purpose being to activate the motor which controls the advancement of the plunger of a temperature-controlled syringe containing oxygen.

With this system, the absorption of oxygen with time is observed by following the motion of the plunger. The time required for the absorption of oxygen to begin is known as the induction time (To). The test is continued until 10 ml of oxygen have been absorbed by the sample, and the corresponding time is indicated by ($T_{10}$ -To). The greater the induction time, the slower is the oxygen consumption, and the more stable is the stabilised polypropylene.

The films used for the test are prepared by dissolving the stabilising compound in benzene and mixing the resultant solution with the powdered polypropylene. The polypropylene is free from any other additive. The solvent is then eliminated by evaporation under reduced pressure, and the resultant powder is pressed into a film having a thickness of about 100 μm, operating at 150° C. and 900 kg/cm², for a time of 2 minutes.

The film is extracted from the press and is cooled rapidly under running water.

Table 1 shows the induction times and the times for absorbing 10 ml of oxygen, both for polypropylene as such and for the polypropylene to which the stabilising compounds XII, VII, VIII and XIV have been added in such quantities as to produce an active nitrogen content of 0.015% by weight in the polymer.

For comparison purposes, films are tested containing the commercial products TINUVIN 770 and CHIMASSORB 944 in such quantities as to again produce an active nitrogen content of 0.015% by weight in the polymer, and also films containing the commercial product CYASORB 5411 in a quantity of 0.5% by weight in the polymer.

TABLE 1

| Additive | Induction time (To) (minutes) | Time for consuming 10 ml of O₂ ($T_{10}$ -To) (minutes) |
|---|---|---|
| None | 480 | 1550 |
| CHIMASSORB 944 | 5000 | 8500 |
| TINUVIN 770 | 7000 | 16000 |
| CYASORB 5411 | 1300 | 1800 |
| COMPOUND XII | 5000 | 13500 |
| COMPOUND VII | 8000 | 19500 |
| COMPOUND VIII | 8000 | 19500 |
| COMPOUND XIV | 8500 | 20000 |

As heretofore described, the reactive stabilising compounds of the present invention can give rise to resinification reactions, or can be anchored to a support or to the polymer to be stabilised, and these characteristics can be utilised in order to enhance the permanence of the stabiliser in the polymer, both during its processing, and during its working life.

The resinification or support-anchoring phenomena, which result in an increase in the permanence of the additive in the polymer, are tested by comparing the stationary concentration of the nitroxyl radical, obtained by oxidising the sterically hindered amino group of the stabilising compound molecule, and measured by ESR spectra taken directly on the polymer samples, to which the stabilising compound has been added either in monomer form, or in resinified form, or supported form, and then heating for some hours to 170° C. Specifically, the formation of the nitroxyl radical takes place directly in the polypropylene film by photo-sensitised oxidation with singlet oxygen. The polypropylene film is obtained as described heretofore. The quantity of stabilising compound introduced into the polymer is 0.15% by weight of the polymer. The photo-sensitiser able to produce singlet oxygen (Rose Bengal, chlorophyll) is added in a quantity of 0.1% by weight with respect to the polymer. The film is then subjected to UV radiation for 18 hours by a high-pressure 150 watt mercury vapour lamp coupled to a UV 31 filter which provides a passing band of radiation of $\lambda \geq 290$ nm. After irradiating a weighed portion of the film, a check is carried out by ESR spectra of the formation of the radical and its persistence in the sample at the temperature of 170° C.

Table 2 shows the test results.

TABLE 2

| Test | Stabilizing compound | Reduction in the radical concentration after 5 hours of heating to 170° C. (% with respect to initial concentration) |
|---|---|---|
| A | COMPOUND VIII | 90% |
| B | COMPOUND VIII plus tin diacetate | 60% |
| C | COMPOUND VIII plus tin dicetate | 30% |
| D | COMPOUND VIII plus tin diacetate | 30% |
| E | COMPOUND VII | 87% |
| F | COMPOUND VII (4 wt % on silica) | 15% | specifically, in tests A and E the stabilising compounds VIII and VII are added respectively in the monomer form to the powdered polymer.

In test B the compound VIII is added to the powdered polypropylene together with the tin diacetate. In test C the procedure is as in test B, but heating the polypropylene film for 1 hour to 80° C. is distilled water.

In test D the compound VII is resinified externally to the polyporpylene in the presence of tin diacetate in a saturated water vapour environment. The resinification produce thus obtained is dissolved in alcohol, and the solution is added to the powdered polypropylene.

The alcohol is then removed by evaporation under reduced pressure, and the residual powder is pressed as heretofore described. In test F, the compound VII anchored to the silica is homogenised with the polypropylene by grinding in a ball mill.

We claim:

1. A stabilized polymer composition comprising a polyolefin and an amount of a product effective to stabilize said polyolefin against degradation from exposure to atmospheric agents and ultraviolet radiation wherein said product is obtained by the hydrolysis and resinification of a reactive stabilizing compound having one of the following formulas

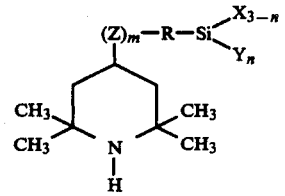

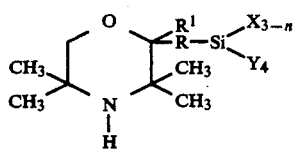

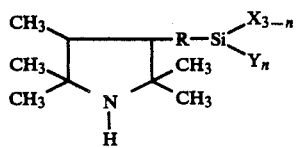

wherein;

m is 0 or 1;

$R^1$ is selected from hydrogen and methyl;

z is selected from

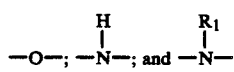

wherein $R_1$ is a linear or branched alkyl group having from 1 to 5 carbon atoms;

R is a linear or branched alkylene group having from 1 to 10 carbon atoms; $-R_2-S-R_3-$; $-R_2-O-R_3$; and

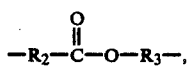

wherein $R_2$ and $R_3$ are each linear or branched alkylene groups having from 2 to 10 carbon atoms;

x is selected from a linear or branched alkyl group having from 1 to 5 carbon atoms;

Y is selected from hydrogen, halogen, $C_1$–$C_4$ acyloxy, $C_1$–$C_4$ alkyloxy, amino, aminooxy and silyloxy; and n is an integer selected from one, two and three.

2. The composition of claim 1 wherein Y is hydrogen.

3. The composition of claim 1 wherein X is methyl and Y is selected from chlorine and $C_1$–$C_4$ alkyloxy.

4. The compositions of claim 1 where the stabilizing compound has the formula

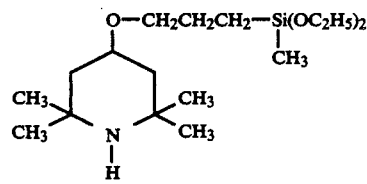

5. The composition of claim 1 wherein the stabilizing compound has the formula

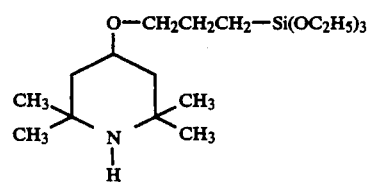

6. The composition of claim 1 wherein the stabilizing compound has the formula

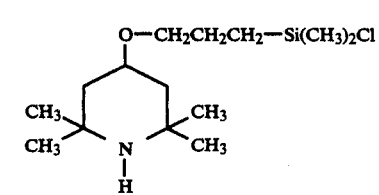

7. The composition of claim 1 wherein the stabilizing compound has the formula

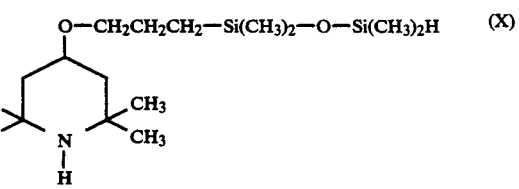

8. The composition of claim 1 wherein the stabilizing compound has the formula

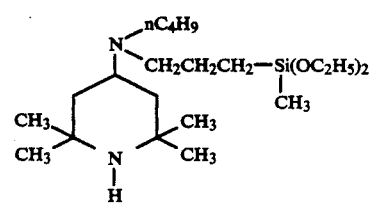

9. The process of claim 1 wherein the stabilizing compound has the formula

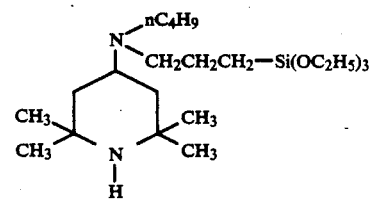

10. The composition of claim 1 wherein the stabilizing compound has the formula

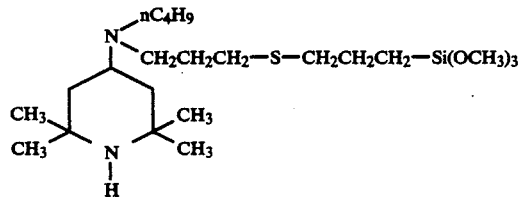

(XV)

11. The composition of claim 1 wherein the stabilizing compound has the formula

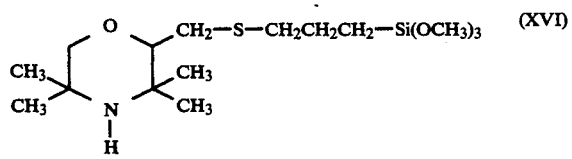

(XVI)

12. The composition of claim 1 wherein the stabilizing compound has the formula

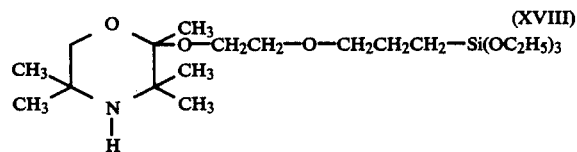

(XVIII)

13. The composition of claim 1 wherein the stabilizing compound has the formula

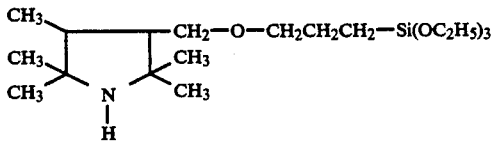

14. The composition of claim 1, wherein hydrolysis and resinification are conducted in the presence of a catalyst selected form zinc octoate, lead maphthenate and tin dibutyllaurate.

15. The composition of claim 14, wherein hydrolysis and resinificati8on are conducted in the presence of a silicone varnish.

16. The composition of claim 1, wherein hydrolysis and resinification of the reactive stabilizing compound occur spontaneously within the organic polymer.

17. The composition of claim 1 fixed to a solid support containing surface hydroxyl groups.

18. The composition of claim 17, wherein the solid support is selected from diatomaceous earth, celite, silica gel, cement, glass, glass fibers and silica-aluminates.

19. The composition of claim 18, wherein the silica gel is made of fumed silica.

20. The composition of claim 1 chemically bound to said organic polymer.

21. The composition of claim 1, wherein the organic polymer is selected from homopolymers of ethylene, propylene and butadiene.

22. The composition of claim 1, wherein the stabilizing compound provides from 0.003% to 0.3% by weight of active nitrogen.

23. The composition of claim 22, wherein the quantity of active nitrogen is in the range of from 0.005% to 0.02% by weight.

* * * * *